United States Patent [19]
Slemon et al.

[11] Patent Number: 5,400,641
[45] Date of Patent: Mar. 28, 1995

[54] TRANSFORMER OIL GAS EXTRACTOR

[75] Inventors: Charles S. Slemon, Encinitas; William M. Lafferty, Leucadia; Anthony E. Diamond, San Diego, all of Calif.

[73] Assignee: Advanced Optical Controls, Inc., Arlington, Va.

[21] Appl. No.: 147,329

[22] Filed: Nov. 3, 1993

[51] Int. Cl.⁶ .................. G01N 1/00; G06F 15/46
[52] U.S. Cl. .................. 73/19.010; 395/22; 395/3
[58] Field of Search .......... 73/19.010; 395/22, 3

[56] References Cited

U.S. PATENT DOCUMENTS

| | | | |
|---|---|---|---|
| 4,330,385 | 5/1982 | Arthur et al. | 73/19.01 |
| 4,474,051 | 10/1984 | Fukuda et al. | 73/19.01 |
| 4,731,732 | 3/1988 | Warchol et al. | 364/510 |
| 4,763,514 | 8/1988 | Naito et al. | 73/19.01 |
| 4,764,344 | 8/1988 | Knab | 422/89 |
| 5,062,292 | 11/1991 | Kanba et al. | 73/19.01 |
| 5,121,443 | 6/1992 | Tomlinson | 382/29 |
| 5,177,994 | 1/1993 | Moriizumi et al. | 395/22 |
| 5,218,440 | 6/1993 | Mathur | 395/22 |
| 5,239,483 | 8/1993 | Weir | 364/497 |
| 5,266,496 | 11/1993 | Dacruz | 436/157 |
| 5,291,607 | 3/1994 | Rustic et al. | 395/750 |

OTHER PUBLICATIONS

Brochure, WEMOS Gas-In-Oil Monitor, Westinghouse Electric Corporation, 1986.
Catalog, Figaro, Figaro Engineering Inc., Aug. 1990.
Brochure, Hydran 201R, Syprotec Inc. 1993.

Primary Examiner—Hezron E. Williams
Assistant Examiner—J. David Wiggins
Attorney, Agent, or Firm—Nydegger & Associates

[57] ABSTRACT

A device is disclosed for extracting dissolved gases from oil in an electrical transformer and for analyzing those gases using a plurality of gas sensors, a signal processor, and a neural network.

14 Claims, 3 Drawing Sheets

TRANSFORMER OIL GAS EXTRACTOR

TECHNICAL FIELD

The present invention is in the field of analyzing dissolved gases in a fluid. Specifically, the invention addresses monitoring the condition of electrical transformers by analysis of dissolved gases in the transformer oil.

BACKGROUND OF THE INVENTION

Electrical power distribution systems distribute electrical power over great distances at high voltages to minimize conductor sizes and compensate for unavoidable transmission losses. When the power is used, it is typically used at much lower voltages than those at which it is distributed. This requires the transformation of the power from a higher voltage to a lower voltage, by means of an electrical transformer. Therefore, for this purpose and many others, there are a great many electrical transformers in service.

Many of these transformers are filled with oil for the purpose of cooling and insulation. As a transformer ages, and as it is subjected to high loads, varying loads, and severe environmental conditions, various components within the transformer will necessarily begin to degrade or eventually to fail. In addition, some defect or misuse can cause failure of some components of the transformer. As components degrade or fail, or as other undesirable processes occur within the transformer, various chemicals can be created in or released into the oil in the transformer. These chemicals can be in the form of dissolved gases, or they can react with other chemicals to form dissolved gases in the transformer oil.

It is well known to periodically sample transformer oil to analyze the dissolved gases to detect the aging or failure of various components, or to detect other processes that might take place within the transformer. The purpose of this analysis is to determine when maintenance, repair, or even replacement of the transformer is necessary. The existence in the transformer oil of a given gas in a given concentration might indicate failure of paper or some other insulator, or it might indicate electrical arcing between components, or it might simply indicate a harmless effect of normal operation. Detecting a single gas dissolved in the oil will seldom reveal a complete and accurate picture of what is happening in the transformer. In order to accurately identify the occurrence of a particular type of problem in the transformer, it is usually necessary to detect the presence and the concentrations of a number of known gases in the oil.

Currently, sampling and analysis of transformer oil is commonly done by sending personnel out to the transformer, drawing a sample of the oil, taking the sample to a laboratory, and running analysis by methods such as gas chromatography to detect the presence and concentrations of the dissolved gases in the oil. In view of the large number of transformers in service, this requires a very large investment in man hours and equipment. It also affects the load capacity of the distribution system involved, and it requires numerous personnel entries into substations and other hazardous areas. Further, information on the dissolved gases present in a given transformer can only be obtained at infrequent intervals, for reasons of economy. Currently known systems are too expensive to be permanently installed on a single transformer, and they would be inherently inaccurate because of an inability to correctly interpret the status of a transformer based on the information that would be available from currently known sensors, without the presence of an operator.

It is an object of the present invention to provide an apparatus for the qualitative and quantitative analysis of the dissolved gases present in a fluid such as the oil in a transformer on a frequent or continuous basis, without the presence of an operator, using inexpensive sensors. It is a further object of the present invention to provide an apparatus for the qualitative and quantitative analysis of the dissolved gases present in transformer oil, that is easy and inexpensive to manufacture and use.

SUMMARY OF THE INVENTION

The preferred embodiment of the present invention, for exemplary purposes, is an apparatus for extracting dissolved gases from the oil in an electrical transformer, and for identifying those gases and their respective concentrations. An oil outlet and an oil return are installed on the transformer to provide access to the oil. Connected to the oil outlet is a gas extraction chamber external to the transformer, for extracting dissolved gases from the oil. Oil flows from the transformer into the extraction chamber under the pressure differential resulting from the hydrostatic head, the gas pressure in the transformer, and a vacuum maintained in the extraction chamber. An oil pump is connected to the gas extraction chamber to return oil to the transformer. A recirculation line from the outlet of the pump returns some of the oil to the gas extraction chamber instead of the transformer when the oil level in the chamber falls to a selected level. The oil upstream of the extraction chamber can be cooled and filtered as required.

The gas extraction chamber is maintained at a partial vacuum. Any gases dissolved in the oil will come out of solution and evolve from the oil into the head space or gas region above the oil in the extraction chamber. A vacuum pump is connected to the gas region in the gas extraction chamber, to evacuate the gas from the chamber. The gases evacuated from the chamber are passed through a gas detection assembly, which contains a plurality of gas sensors. Gases evacuated from the chamber are returned to the chamber, in a continuous loop, to establish an equilibrium of gas concentrations at the sensors, which match the gas concentrations in the chamber. Makeup air is added as required to maintain an oxygen presence in the chamber as required by some sensors.

Each sensor is subjected to a plurality of levels of biasing voltage. At each level of the biasing voltage, a given level of the output signal from a given sensor identifies a certain set of gases which are possibly present and the concentration of each gas which, if present alone in air at Standard Temperature and Pressure (STP), would produce the given level of the output signal. However, the sensor can not sense which gases are actually present and which are not. Some sensors can be subjected to varying bias by varying the level of oxygen present or the humidity.

The different gas sensors are able to sense intersecting sets of gases, in overlapping ranges of concentrations. The output signals from all of the gas sensors at all of the bias voltage levels are fed into a pattern recognizer such as a neural network or a fuzzy logic analyzer to identify the gases present, and their concentrations, based upon the characteristics of the combined signals.

The pattern recognizer or neural network is conditioned to interpret the combined signals, to identify the gases and their concentrations, by being fed a number of examples of the combined signals, with each example being correlated to the presence of known gases in known concentrations.

This invention is applicable to analysis of dissolved gases in many types of fluids, not limited to the transformer oil addressed by the preferred embodiment.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

There are seven known gases that are commonly used as indicators of the condition and status of a transformer. They are hydrogen, methane, carbon monoxide, carbon dioxide, ethylene, ethane, and acetylene. There are also a number of known background gases which may be present, but which are not commonly used as indicators. Sensors are commercially available for qualitative and quantitative detection of these gases, at a reasonable cost. An example of such a sensor is the TGS Electrochemical Sensor available from Figaro, Inc. These sensors and other similar ones can identify a plurality of gases as possibly being present in a gas sample, including the gases of interest here. Each sensor is subjected to a variable bias voltage, and each has an output signal in the form of an electrical resistance which can be read by known means. For each gas indicated as possibly present by a given sensor output signal at a given bias voltage, the theoretical concentration of that gas, alone in air, is also identified. However, for a given sensor, at a given bias voltage, a given resistance reading will only indicate that a number of different identified gases may be present, with a theoretical concentration being given for each gas. The reading will not indicate which gases are actually present and which are not. Furthermore, if more than one gas is actually present, the actual concentration of each gas is different from the theoretical concentration indicated for that gas, if it alone were present.

Figure 1:
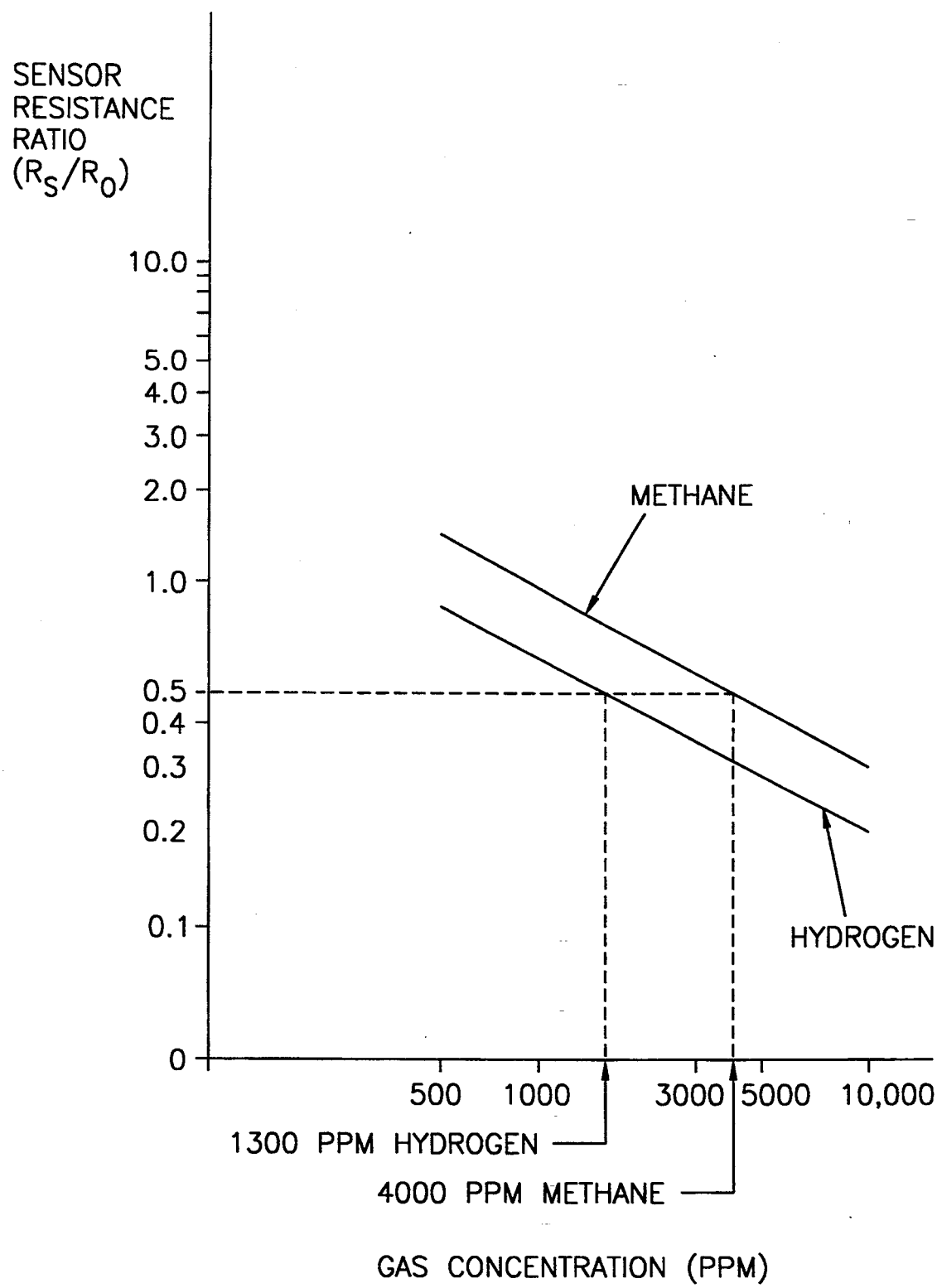
FIG. 1 is a graph of the output signal of a gas sensor versus gas concentrations, at a given bias voltage, for several gases.

FIG. 1 is a graph which illustrates the types of gases which might be identified, and the representative concentrations of these gases which might be identified, for a given sensor, at a given bias voltage. The graph shows the ratio of actual sensor signal to a reference signal, over a range of gas concentrations. For illustration purposes in this graph, the sensor output is calibrated to show a reference resistance reading, designated $R_0$, for methane at 1000 ppm in air, at a given bias voltage. When the sensor is subjected to the same bias voltage and exposed to methane in air at concentrations ranging from 500 ppm to 10,000 ppm, the actual output signal of the sensor, designated $R_s$, ranges from approximately 1.3 $R_0$ to approximately 0.3 $R_0$. It can be seen that, for this sensor, at the given bias voltage, a methane concentration in air of approximately 4000 ppm will yield an actual output signal of approximately 0.5 $R_0$. However, the same actual output signal from the same sensor at the same bias voltage also identifies the possible presence of hydrogen, at a theoretical concentration in air of approximately 1300 ppm. Therefore, the sensor being illustrated is identifying a set of gases possibly present, methane and hydrogen. Since it is not known which gas is present, or whether both are present in an unknown ratio, the sensor is also identifying a range of possible concentrations of each gas. Therefore, this reading can not be relied upon to qualitatively or quantitatively identify any gas as actually being present, or having any actual concentration. In actual practice, each output signal usually indicates the possible presence of more than two gases, so the illustration given here is simpler than the situation normally encountered.

Figure 2:
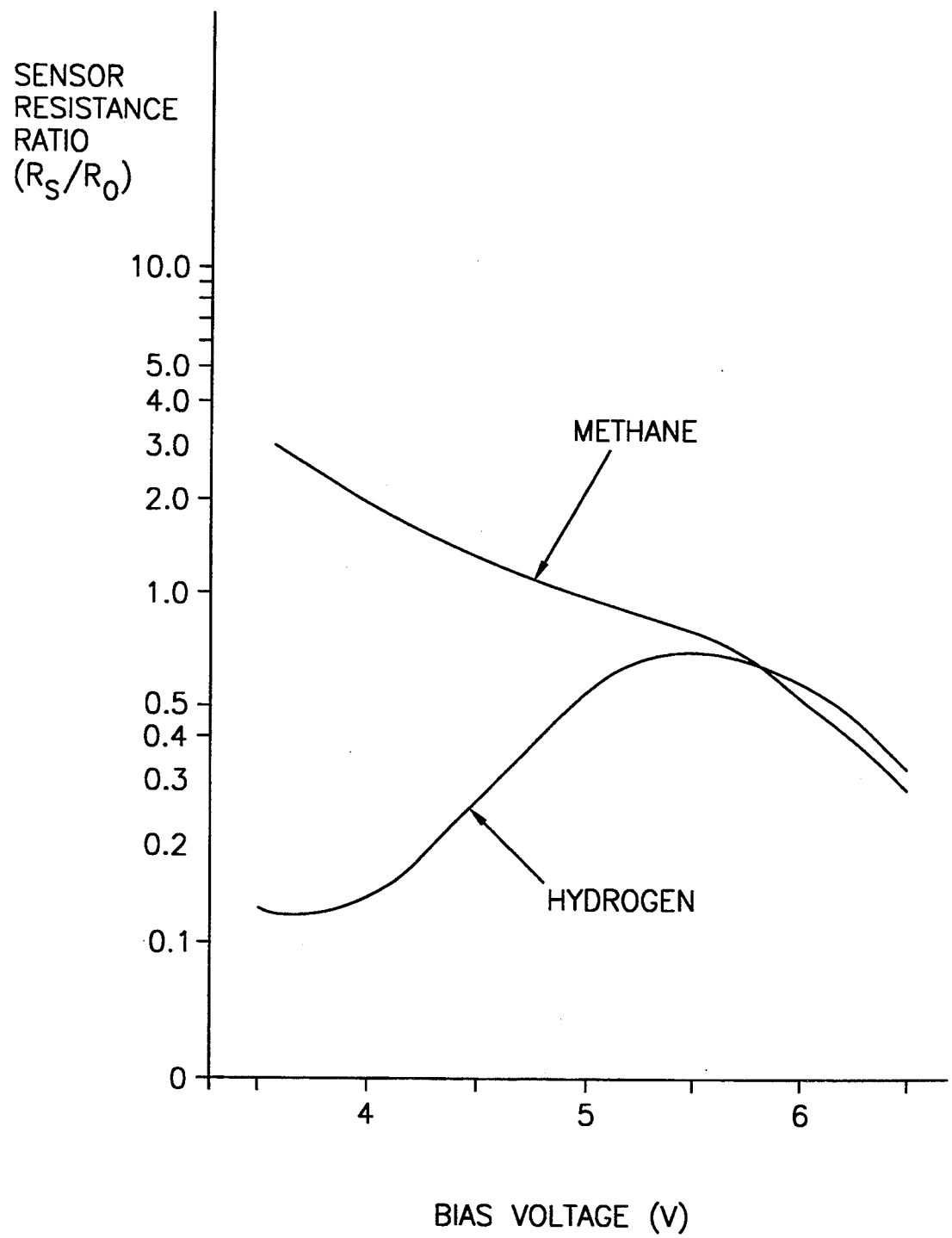
FIG. 2 is a graph of the output signal of a gas sensor versus bias voltage, at a given gas concentration, for several gases.

Another variable is introduced by varying the bias voltage placed upon the sensor, thereby controlling the sensor temperature. FIG. 2 is a graph illustrating the effect of varying the bias voltage on a given sensor exposed to a given concentration of a known gas. The two curves on the graph represent the typical sensor response for each of the two gases discussed above. Each curve shows how the sensor resistance reading varies with bias voltage, in a given concentration of the applicable gas. It can be seen that if the bias voltage is approximately 4 volts, the sensor response to a given mixture of the two gases is far different from what it would be if the bias voltage is approximately 6 volts. Response curves for the other gases of interest are similarly diverse, further complicating the analysis of gases present in a given sample. Other biasing influences can be imposed upon some sensors by varying the level of oxygen present or the relative humidity.

It can be seen that if such a sensor were simply installed so as to be exposed to the gases, analysis of a signal received would yield very little useful information about the identity and concentrations of gases actually present, even if the bias voltage were accurately controlled. A variety of such sensors are available, with a variety of response characteristics. Each type of sensor views the gases actually present from a plurality of different parametric perspectives, thereby resulting in a different set of response characteristics for each different gas. The sensors can be selected to yield information about overlapping sets of gases, and they can have overlapping sensitivity ranges to those gases. Still further, as noted above, varying the bias voltage on a given sensor will alter its response characteristics. The output of such sensors can be extremely complex, exceeding the analysis capability of conventional computer systems. Even if such complex signals could be interpreted by conventional computer methods, this would not solve the problem of having to draw samples and take them to a laboratory for analysis.

The present invention recognizes that exposing a plurality of such sensors to the dissolved gases will yield a plurality of diverse signals from a plurality of parametric perspectives which, if properly interpreted, can adequately identify the gases actually present in transformer oil and adequately identify the concentration of each. As in many commercial or industrial applications, it is not necessary in this application to identify gas concentrations to a degree of accuracy normally required for scientific research. It is instead adequate to identify the gases and their concentrations with a lesser degree of accuracy required to plan the effective maintenance or replacement of the transformer. The adequate degree of accuracy must be selected by the users of the resultant information.

The more sensors used, the more information will be available to contribute to the adequacy of the results of the signal interpretation. Varying the bias voltage on each sensor and taking readings at each level of bias voltage can also provide additional signals from additional parametric perspectives, thereby increasing the reliability of the interpretation achieved. This extremely complex set of sensor output signals, although not susceptible to known algorithmic analysis methods, is susceptible to analysis by high order pattern recognition methods. Such methods are practiced by the use of neural networks and fuzzy logic processors.

The present invention utilizes the high order pattern recognition capability of a commercially available neural network to interpret the convoluted signals received from a plurality of diverse gas sensors, with each sensor being subjected to a plurality of bias voltage levels, and with a resistance reading being taken from each sensor at each bias voltage level. A plurality of signal sets, each representing a known set of gases at known concentrations, are fed into the neural network, and the proper interpretation of each signal set is identified for the network. This conditions the neural network to recognize patterns in the signals which qualitatively and quantitatively identify known sets of gases at known concentrations. Each resistance reading taken from each sensor at each bias voltage level is processed by known methods into a voltage signal and converted by an analog to digital converter, then fed into the neural network as a digital signal. If desired, the signals received from the sensors can be pre-processed, to reduce the number of signals fed into the neural network to a smaller number, by eliminating redundant signals, by truncating the signal spectrum at the top or bottom, or by applying a number of other common criteria, depending upon the sensors or the neural network used.

Figure 3:
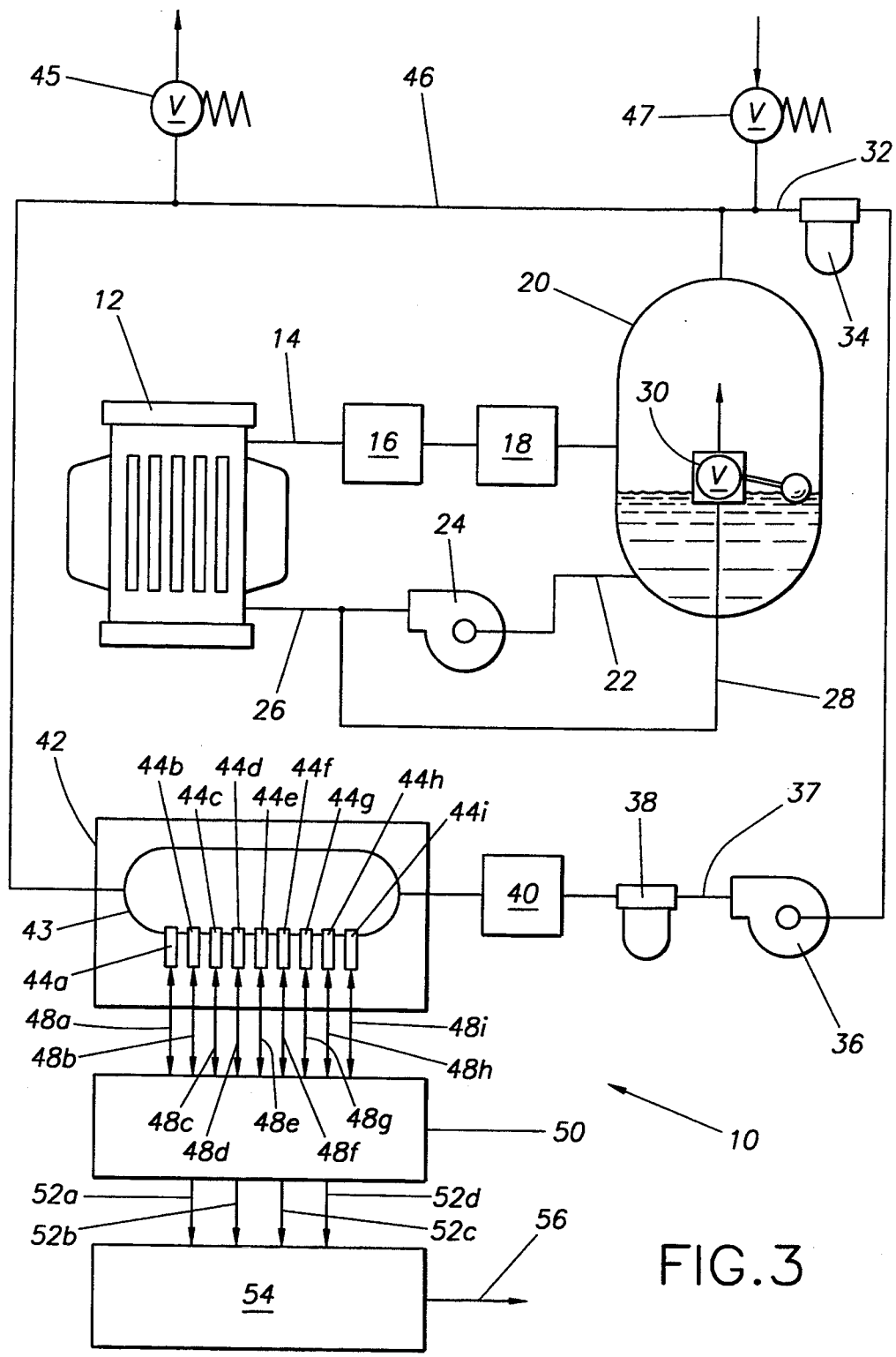
FIG. 3 is a schematic diagram of the apparatus of the present invention.

FIG. 3 is a schematic of the analysis device 10 of the present invention, illustrating how the gases are separated from the transformer oil, how the sensors are exposed to the gases, and how the sensor signals are interpreted. Transformer 12 has an oil outlet pipe 14 which conducts the transformer oil through an oil cooler 16 and a filter 18 and on to a gas extraction chamber 20. The oil is returned to transformer 12 via an oil pump suction pipe 22, an oil pump 24, and a transformer return pipe 26. Instead of returning to transformer 12, some of the oil can be returned to extraction chamber 20 via a recirculation pipe 28, under the control of a float valve 30, to maintain a minimum level of oil in extraction chamber 20.

The head space at the top of extraction chamber 20 is attached by a gas suction pipe 32 to a chamber oil trap 34 and to the suction of a vacuum pump 36. A make-up air valve 47 is connected to suction pipe 32. The outlet of vacuum pump 36 is connected via a vacuum pump outlet pipe 37 to a pump oil trap 38 and a gas cooler or drier unit 40, and finally to a gas analyzer cabinet 42. Within gas analyzer cabinet 42, pipe 37 connects to a gas analysis chamber 43, which is in turn connected by a gas recirculation pipe 46 to the head space of gas extraction chamber 20. A vent valve 45 is connected to recirculation pipe 46. A gas chromatograph or infrared spectrometer can be connected in parallel to analysis chamber 43, to provide inputs for the pattern recognition unit.

Within gas analysis chamber 43, nine gas sensors 44a through 44i are exposed to the contents of the gas in the head space of extraction chamber 20. The input/output cables 48a through 48i of sensors 44a through 44i, respectively, are connected to a processor 50. Processor 50 can be one of various types of microprocessors commercially available, for applying a selected bias voltage to each of the sensors 44a through 44i, and for reading the output resistance signal of each sensor. Processor 50 also is capable of incrementally changing each bias voltage in a programmed sequence, receiving each corresponding sensor signal, and sorting or otherwise modifying the sensor signals into desired numerical value signal segments, according to a programmed protocol which is selected to suit the particular sensors and neural network used. It should be recognized that processor 50 may simply pass all sensor signals on, after conversion to numerical signals, without any sorting or other modification, if appropriate. The resulting signal segments produced by processor 50 are passed by leads 52a through 52d to a neural network 54.

Neural network 54 is one of various well known types which receives a plurality of numerical signals and interprets them to produce a desired output signal, which in this case, will identify gases present and identify the concentration of each gas. Neural network 54 is conditioned to properly interpret the signals received by having a plurality of signal sets entered, with each signal set being correlated with a desired output signal identifying the gases present and their respective concentrations. The signal sets used for conditioning purposes are generated by exposing the sensors to selected sets of gas constituencies, given the characteristics of the sensors to be used, and given the pre-processing function programmed into processor 50. After neural network 54 has been conditioned by a sufficient number of signal sets, neural network 54 will be capable of sufficiently recognizing patterns of signal segment characteristics to generate an output signal at lead 56 to adequately identify the gases present and their respective concentrations.

OPERATION

After analysis device 10 has been installed at the transformer, oil pump 24 is operated either continuously or periodically to maintain a selected oil level in extraction chamber 20. Dissolved gases will come out of solution and evolve from the oil. The oil flow rate can be selected according to the anticipated level of gases present. If gas concentration is low, a higher oil flow rate can be used, and vice versa. While oil is being circulated, vacuum pump 36 is operated to evacuate the gases from the head space of extraction chamber 20, above the oil. The gases evacuated are passed through analysis chamber 43 and some are circulated back to the head space of extraction chamber 20. Makeup air can be added by known means, and gas can be vented by known means. Eventually, recirculation of the gases through this loop will cause the gas concentrations in analysis chamber 43 to reach equilibrium with the concentrations in extraction chamber 20, so that sensors 44a through 44i are exposed to the true concentration of gases which have evolved from the oil.

Processor 50 will impose a selected number of levels of bias voltage on sensors 44a through 44i and read the output signal from each sensor at each level of bias voltage. For example, 255 levels of bias voltage can be sequentially applied to each of the nine sensors 44a through 44i, resulting in 2295 sensor output signals. Processor 50 can then sort these signals according to a programmed scheme suited to the sensors, possibly discarding redundant signals, possibly selecting information on certain gases only from certain sensors. Such a scheme might result, for example, in the generation of 148 signal segments corresponding to 20 segments each from 5 sensors 44a through 44e, and 12 segments each from 4 sensors 44f through 44i.

Each signal segment might correspond directly to a sum of signals from a sensor, for example, or the segment might correspond to a possible range of concentrations for a given gas calculated from a limited number of signals received from certain sensors. As a more specific example, it might be known that if sensor 44a yields resistances above a certain level at all bias voltages in a certain range, this indicates with relative certainty that methane is present at a concentration above 10,000 ppm. This knowledge might significantly reduce the level of interpretation required by neural network 54, so the output of sensor 44a at the pertinent bias voltages might be designated as one of the signal segments fed into neural network 54. The most advantageous designation of the signal segments to reduce, in processor 50, the interpretation burden on neural network 54 will depend upon a multitude of similar factors which may be known about the sensors selected and the gases sought. Empirical testing of device 10 can be used to verify the advantageous designation of signal segments.

The signal segments produced by processor 50 are fed into neural network 54, which will sufficiently recognize a pattern or a plurality of patterns of signal segments to produce an output signal which adequately identifies the gases present and their respective concentrations. The signal produced by neural network 54 can be stored in local memory or transmitted to a remote monitoring facility by a modem and a telephone line.

While the particular TRANSFORMER OIL GAS EXTRACTOR as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A device for qualitatively and quantitatively identifying the constituents of dissolved gas in a fluid, comprising:
   a reservoir of the fluid and gas solution, said fluid reservoir having an outlet;
   an extraction means connected in fluid flow communication with said reservoir outlet for extracting gas from the fluid;
   a sensing means connected in fluid flow communication with said extraction means, said sensing means comprising a plurality of gas sensors exposed to the gas, each of said gas sensors having an output signal, the level of said output signal being variable over a known range for a given concentration of a given constituent, wherein each of said gas sensors is subjected to a variable applied voltage causing each said sensor to generate, at each level of voltage, a resistance signal which indicates the possible presence of a plurality of identified constituents at identified concentrations specific for each defined gas that each said sensor is known to be sensitive toward;
   a control means for controlling said variable voltage level applied to said sensors; and
   an interpretation means communicatively connected for receiving and interpreting said output signals to identify the constituents of the gas and their respective concentrations by performing a multiple stage comparison between said signals and a known set of sensor responses for each gas sensor type, for each gas species type, over the applied voltage range, and over the applicable temperature range, as a function of each gas type concentration, said interpretation means being conditioned to recognize patterns of said sensor responses by exposure to said known set of responses under said known conditions.

2. A device as claimed in claim 1, wherein said gas extraction means comprises:
   a gas extraction chamber through which the fluid is circulated, said chamber being at a sufficiently low pressure to allow the gas to evolve from the fluid; and
   a vacuum pump attached in fluid flow communication with said gas extraction chamber to evacuate the gas from said chamber.

3. A device as claimed in claim 1, further comprising a signal conditioning means for conditioning said output signals prior to receipt of said output signals by said interpretation means.

4. A device as claimed in claim 3, wherein said signal conditioning means combines said output signals into a convoluted signal segment.

5. A device as claimed in claim 3, wherein said signal conditioning means segregates said output signals into a plurality of signal segments, the count of said signal segments being fewer in number than the number of said output signals.

6. A device for qualitatively and quantitatively identifying dissolved gases in a fluid, comprising:
   a gas extraction chamber in fluid flow communication with a supply of the fluid;
   a vacuum pump connected to said extraction chamber to evacuate gases therefrom;
   a plurality of gas sensors exposed to the gases evacuated from said extraction chamber, each of said sensors having an output signal, the level of said output signal being variable over a known range for a given concentration of a given gas, wherein each of said gas sensors is subjected to a variable applied voltage causing each said sensor to generate, at each level of voltage, a resistance signal which indicates the possible presence of a plurality of identified gases at identified concentrations specific for each defined gas that each said sensor is known to be sensitive toward;
   a control means for controlling said variable voltage level applied to said sensors; and
   a signal interpretation means for receiving and interpreting said output signals to identify the gases extracted from said fluid and their respective concentrations by performing a multiple stage comparison between said signals and a known set of sensor responses for each gas sensor type, for each gas species type, over the applied voltage range, and over the applicable temperature range, as a function of each gas type concentration, said interpretation means being conditioned to recognize patterns of said sensor responses by exposure to said known set of responses under said known conditions.

7. A device as claimed in claim 6, further comprising a signal conditioning means for conditioning said output signals prior to receipt of said output signals by said signal interpretation means.

8. A device as claimed in claim 7, wherein said signal conditioning means combines said output signals into a convoluted signal segment.

9. A device as claimed in claim 7, wherein said signal conditioning means segregates said output signals into a plurality of signal segments, the count of said signal segments being fewer in number than the number of said output signals.

10. A device for qualitatively arid quantitatively identifying dissolved gases in the oil in an electrical transformer, comprising:
a gas extraction chamber connected to an oil outlet on the transformer to receive oil therefrom;
an oil pump connected to said extraction chamber to return oil therefrom to the transformer;
a vacuum pump connected to said extraction chamber to evacuate gases therefrom;
a plurality of gas sensors exposed to the gases evacuated from said extraction chamber, each of said sensors having an output signal, the level of said output signal being variable over a known range for a given concentration of a given gas, wherein each of said gas sensors is subjected to a variable applied voltage causing each said sensor to generate, at each level of voltage, a resistance signal which indicates the possible presence of a plurality of identified gases at identified concentrations specific for each defined gas that each said sensor is known to be sensitive toward;
a signal conditioning means for conditioning said sensor output signals for interpretation;
a control means for controlling said variable voltage level applied to said sensors; and
a neural network for receiving and interpreting said conditioned signals to identify the gases extracted from the transformer oil and their respective concentrations by performing a multiple stage comparison between said signals and a known set of sensor responses for each gas sensor type, for each gas species type, over the applied voltage range, and over the applicable temperature range, as a function of each gas type concentration, said interpretation means being conditioned to recognize patterns of said sensor responses by exposure to said known set of responses under said known conditions.

11. A device as claimed in claim 10, wherein said signal conditioning means combines said output signals into a convoluted signal segment.

12. A device as claimed in claim 10, wherein said signal conditioning means segregates said output signals into a plurality of signal segments, the count of said signal segments being fewer in number than the number of said output signals.

13. A device for qualitatively and quantitatively identifying the constituents of dissolved gas in a fluid, comprising:
a reservoir of the fluid and gas solution, said fluid reservoir having an outlet;
an extraction means connected in fluid flow communication with said reservoir outlet for extracting gas from the fluid;
a plurality of sensing means connected in fluid flow communication with said extraction means, said sensing means being exposed to the gas, each of said sensing means having an output signal, the level of said output signal being variable over a known range for a given concentration of a given constituent, wherein each level of each output signal from each sensing means indicates the possible presence of a plurality of identified constituents at identified concentrations specific for each defined gas that each said sensor is known to be sensitive toward;
an interpretation means communicatively connected for receiving and interpreting said output signals to identify the constituents of the gas and their respective concentrations by performing a multiple stage comparison between said signals and a known set of sensor responses for each sensing means, for each gas species type, over the applied voltage range, and over the applicable temperature range, as a function of each gas type concentration, said interpretation means being conditioned to recognize patterns of said sensor responses by exposure to said known set of responses under said known conditions; and
a signal conditioning means for conditioning said output signals prior to receipt of said output signals by said interpretation means, wherein said signal conditioning means combines said output signals into a convoluted signal segment.

14. A device for qualitatively and quantitatively identifying the constituents of dissolved gas in a fluid, comprising:
a reservoir of the fluid and gas solution, said fluid reservoir having an outlet;
an extraction means connected in fluid flow communication with said reservoir outlet for extracting gas from the fluid;
a plurality of sensing means connected in fluid flow communication with said extraction means, said sensing means being exposed to the gas, each of said sensing means having an output signal, the level of said output signal being variable over a known range for a given concentration of a given constituent, wherein each level of each output signal from each sensing means indicates the possible presence of a plurality of identified constituents at identified concentrations specific for each defined gas that each said sensor is known to be sensitive toward;
an interpretation means communicatively connected for receiving and interpreting said output signals to identify the constituents of the gas and their respective concentrations by performing a multiple stage comparison between said signals and a known set of sensor responses for each sensing means, for each gas species type, over the applied voltage range, and over the applicable temperature range, as a function of each gas type concentration, said interpretation means being conditioned to recognize patterns of said sensor responses by exposure to said known set of responses under said known conditions; and
a signal conditioning means for conditioning said output signals prior to receipt of said output signals by said interpretation means, wherein said signal conditioning means segregates said output signals into a plurality of signal segments, the count of said signal segments being fewer in number than the number of said output signals.

* * * * *